United States Patent
Chang et al.

(10) Patent No.: US 6,620,971 B2
(45) Date of Patent: Sep. 16, 2003

(54) ASYMMETRIC β-KETOIMINATE LIGAND COMPOUND, PREPARATION METHOD THEREOF, AND ORGANOMETAL PERCURSOR COMPRISING THE SAME

(75) Inventors: Seok Chang, Daejun-Shi (KR); Soon Taik Hwang, Daejun-Shi (KR); Euk Che Hwang, Daejun-Shi (KR)

(73) Assignee: Samsung Electronics Co., Ltd., Kyungki-Do (KR)

( * ) Notice: Subject to any disclaimer, the term of this patent is extended or adjusted under 35 U.S.C. 154(b) by 0 days.

(21) Appl. No.: 10/051,086

(22) Filed: Jan. 22, 2002

(65) Prior Publication Data

US 2002/0156325 A1 Oct. 24, 2002

(30) Foreign Application Priority Data

Jan. 30, 2001 (KR) .................... 2001-0004292

(51) Int. Cl.$^7$ ............... C07C 323/23; C07C 225/14
(52) U.S. Cl. ............... 564/502; 564/278; 564/279; 564/471; 564/472
(58) Field of Search .................. 564/278, 279, 564/471, 472, 502

(56) References Cited

U.S. PATENT DOCUMENTS

| | | | |
|---|---|---|---|
| 2,198,260 A | * 4/1940 | van Melsen | 260/584 |
| 3,141,880 A | * 7/1964 | Martin | 260/247.7 |
| 3,388,141 A | * 6/1968 | Berenbaum | 260/439 |
| 4,950,790 A | 8/1990 | Norman | |

FOREIGN PATENT DOCUMENTS

JP 2-298714 * 10/1994 ......... C07C/251/08
JP 6-298714 10/1994

OTHER PUBLICATIONS

Database CAPLUS on STN, Acc. No. 1993:685030, Schulz et al., Chemistry of Materials (1993), 5(11), p. 1605–17 (abstract).*
Database CAPLUS on STN, Acc. No. 2001:183247,Edleman et al., Materials Research Society Symposium Proceedings (2000), 623 (Materials Science of Novel Oxide–Based Electronics), p. 371–76 (abstract).*

* cited by examiner

*Primary Examiner*—Brian Davis
(74) *Attorney, Agent, or Firm*—Birch, Stewart, Kolasch & Birch, LLP

(57) ABSTRACT

An asymmetric β-ketoiminate ligand compound, represented by the following chemical formula (4):

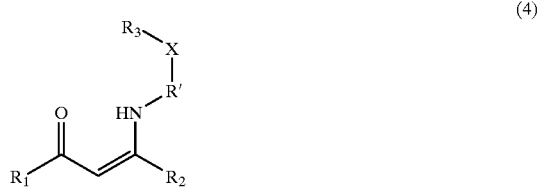

(4)

wherein, $R_1$ is a linear or branched alkyl group containing 1 to 8 carbon atoms; $R_2$ is a linear or branched alkyl group containing 2 to 9 carbon atoms, with the proviso that $R_2$ contains more carbon atoms than $R_1$; R' is a linear or branched alkylene group containing 1 to 8 carbon atoms or a hydrocarbon containing 1 to 3 ethylene ether or propylene ether moieties, represented by —$(CH_2)_nO$— (n=2 or 3); $R_3$ is a hydrogen atom or a linear or branched alkyl group containing 1 to 9 carbon atoms; and X is an oxygen atom or a sulfur atom.

4 Claims, 2 Drawing Sheets

ASYMMETRIC β-KETOIMINATE LIGAND COMPOUND, PREPARATION METHOD THEREOF, AND ORGANOMETAL PERCURSOR COMPRISING THE SAME

BACKGROUND OF THE INVENTION

1. Field of the Invention

The present invention relates to an asymmetric β-ketoiminate ligand compound. More particularly, the present invention relates to an asymmetric β-ketoiminate ligand compound, which is excellent in terms of chemical stability, thermal properties, and solubility in organic solvents. Also, the present invention is concerned with a method for preparing the ligand compound and with an organometallic precursor containing the ligand compound, suitable for use in chemical vapor deposition.

2. Description of the Prior Art

For use as dielectric thin films, ferroelectric thin films, electrodes, etc., metal oxide films are formed by various deposition methods which are representatively exemplified by sputtering technique, sol-gel technique, and chemical vapor deposition technique. Using volatile organometallic compounds as sources for metal oxide films, chemical vapor deposition methods have attracted keen attention owing to their advantages of high deposition rate, deposition uniformity over large areas, excellent step coverage, and easy control of metal composition ratio (See: Adv. Materials for Optics and Electronics, 1993, 2, 271).

Use of excellent precursors meeting certain standards is a prerequisite for success in the preparation of thin films through chemical vapor deposition. Useful precursors are required to exhibit outstanding thermal and chemical stability, excellent evaporation or sublimation properties, low chemical toxicity, large difference between evaporation and decomposition temperatures, and no reactivity with other compounds in a reactor during evaporation or delivery in gas phases. Additionally, in order to obtain a multi-component thin film of high quality, composition ratio of individual metal components introduced into the thin film must be easy to control and their respective precursors must be similar to one another in decomposition behavior at a deposition temperature.

Some recent studies into precursors for use in chemical vapor deposition have been performed with M(β-diketonate)$_n$ precursors using β-diketone as a ligand and with M(OR)$_x$ (β-diketonate)$_y$ precursors using alcohol and β-diketone as co-ligands. However, these precursors are discovered to have drawbacks in aspects of volatility, formation of residues after evaporation, instability to moistures, and reactivity with other precursors. When preparing multi-component metal oxide thin films, such as BST (barium strontium titanate), by use of such precursors, the great difference between the volatilization properties of a titanium precursor and of barium and strontium precursors makes the chemical vapor deposition difficult.

There have been reported precursors using β-ketoimine ligands in which one of the oxygen atoms of β-diketone is substituted with a nitrogen atom. For example, precursors represented by M$^{n+}$(β-ketoiminate) n are disclosed in U.S. Pat. No. 4,950,790. Employing β-ketoiminate as a ligand, these precursors are improved in thermal and chemical stability, but poor in resistance to hydrolysis.

Japanese Pat. Laid-Open Publication No. Hei. 6-298,714 introduces the use of N-alkoxy-β-ketoimine as a ligand, teaching that metal complexes can be prepared by reacting a symmetric ligand having a group, such as —CF$_3$ or t-butyl, substituted at both ends of β-ketoimine, or an asymmetric ligand of –1 equivalent having a substituent only at a carbon of the ketone half with +2 equivalent metal such as Ba, Ca and so forth. The N-alkoxy-β-ketoimine can be obtained by an ordinary preparation method for β-ketoimines in which substituted β-diketone is reacted with amine alcohol in the presence of an acid catalyst.

For the convenience of chemical vapor deposition, precursors are generally delivered in liquid phases. Because this liquid delivery chemical vapor deposition commonly employs n-butyl acetate as a solvent, the solubility of precursors for liquid delivery chemical vapor deposition in the solvent is of particular importance. A precursor which has a low solubility in n-butyl acetate may cause the problem of clogging the delivery pipe only after several uses thereof in the preparation of thin films. This problem is also caused upon using N-alkoxy-β-ketoiminate type ligands in the preparation of the precursor, although they improve the stability of the precursor.

Therefore, there remains a need for a ligand that can be used to produce a precursor which is highly soluble in such a solvent in addition to exhibiting excellent thermal and chemical stability, excellent evaporation or sublimation properties, low chemical toxicity, large difference between evaporation and decomposition temperatures, and no reactivity with other compounds during evaporation or delivery in gas phases.

SUMMARY OF THE INVENTION

Leading to the present invention, the intensive and thorough research into organometallic precursors for chemical vapor deposition resulted in the finding that modification of N-alkoxy-β-ketominate ligands in such a way as for the imine half of the β-kotomine backbone to bear more carbon atoms than the ketone half produces novel aymmetric ligands which can be used to produce precursors highly soluble in general organic solvents including n-butyl acetate.

Therefore, it is an object of the present invention to overcome the above problems encountered in prior arts and to provide a β-ketoiminate ligand which is greatly increased in solubility, as well as showing excellent evaporation properties and thermal and chemical stability.

In accordance with an aspect of the present invention, there is provided an asymmetric β-ketoiminate ligand compound represented by the following chemical formula (4):

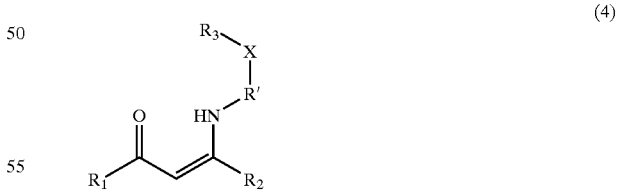

(4)

wherein, R$_1$ is a linear or branched alkyl group containing 1 to 8 carbon atoms; R$_2$ is a linear or branched alkyl group containing 2 to 9 carbon atoms, with the proviso that R$_2$ contains more carbon atoms than R$_1$; R' is a linear or branched alkylene group containing 1 to 8 carbon atoms or a hydrocarbon containing 1 to 3 ethylene ether or propylene ether moieties, represented by —(CH$_2$)$_n$O— (n=2 or 3); R$_3$ is a hydrogen atom or a linear or branched alkyl group containing 1 to 9 carbon atoms; and X is an oxygen atom or a sulfur atom.

In accordance with another aspect of the present invention, there is provided a method for preparing the asymmetric β-ketoiminate ligand compound, comprising the step of reacting an α,β-yne-one compound, represented by the following chemical formula (1) with a primary amine represented by the following chemical formula (2) or with a secondary amine represented by the following chemical formula (3):

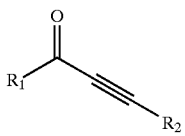
(1)

$R_3X—R'—NH_2$ (2)

$(R_3X—R')_2—NH$ (3)

wherein, $R_1$ is a linear or branched alkyl group containing 1 to 8 carbon atoms; and $R_2$ is a linear or branched alkyl group containing 2 to 9 carbon atoms, with the proviso that $R_2$ contains more carbon atoms than $R_1$; R' is a linear or branched alkylene group containing 1 to 8 carbon atoms or a hydrocarbon containing 1 to 3 ethylene ether or propylene ether moieties, represented by —$(CH_2)_nO$— (n=2 or 3); $R_3$ is a hydrogen atom or a linear or branched alkyl group containing 1 to 9 carbon atoms; and X is an oxygen atom or a sulfur atom.

DETAILED DESCRIPTION OF THE INVENTION

Figure 1:
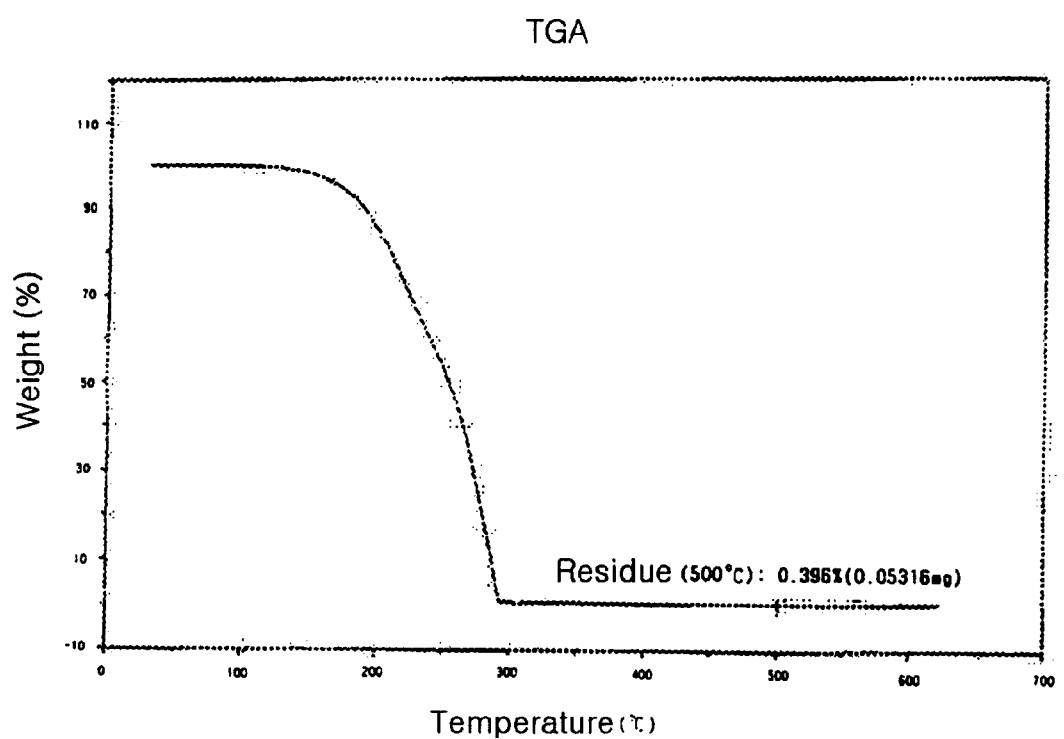
FIG. 1 is a graph showing the thermal properties of the metal complex of Example 4 as analyzed by thermal gravimetry.

By the reaction of substituted β-diketone with amine alcohol in the presence of an acid catalyst, it is impossible to synthesize a desired asymmetric ligand compound of the present invention, which contains more carbon atoms in its imine half than in its ketone half, because carbons in the ketone half are substituted.

In accordance with the present invention, α,β-yne-one containing at least 6 carbon atoms, represented by the following chemical formula (1):

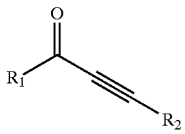
(1)

wherein, $R_1$ is a linear or branched alkyl group containing 1 to 8 carbon atoms; and $R_2$ is a linear or branched alkyl group containing 2 to 9 carbon atoms, with the proviso that $R_2$ contains more carbon atoms than $R_1$, is reacted with a primary amine represented by the following chemical formula (2) or with a secondary amine represented by the following chemical formula (3):

$R_3X—R'—NH_2$ (2)

$(R_3X—R')_2—NH$ (3)

wherein, R' is a linear or branched alkylene group containing 1 to 8 carbon atoms or a hydrocarbon containing 1 to 3 ethylene ether or propylene ether moieties, represented by —$(CH_2)_nO$— (n=2 or 3); $R_3$ is a hydrogen atom or a linear or branched alkyl group containing 1 to 9 carbon atoms; and X is an oxygen atom or a sulfur atom, to provide an asymmetric β-ketoimine represented by the following chemical formula (4):

(4)

wherein, $R_1$, $R_2$, R', $R_3$, and X are as defined above.

Based on a β-ketoimine backbone, the ligand compounds of the present invention are characterized by the asymmetry in which carbon atoms in the imine half number more than in the ketone half.

The asymmetric β-ketoimine ligand of the chemical formula (4) where $R_3$ is an alkyl group forms a metal complex represented by $ML_2$ wherein M stands for a metal ion and L for the ligand, with Ca, Sr or Ba, and a metal complex represented by $ML_3$ with V, Nb or Ta. When meeting with a metal element belonging to Group IV of the Periodic Table, such as Ti, Zr or Hf, on the other hand, the asymmetric β-ketoimine ligand having a hydrogen atom for $R_3$ forms a metal complex represented by $ML_2$, taking a charge number of −2.

With high solubility in general organic solvents as well as in n-butyl acetate extensively used in liquid delivery chemical vapor deposition method, the metal complexes of the asymmetric β-ketoimine ligands of the present invention are very useful as organometallic precursors for production of thin films by the method.

Additionally, use of the metal complexes of the present invention enjoys the advantage of guaranteeing similar evaporation and decomposition behaviors among precursors required for the deposition of multi-component metal oxide thin films. Generally, when forming multi-component thin films through chemical vapor deposition, excess metal precursors with relatively high volatility must be supplied in order to control the composition of the thin films because not only the evaporation temperatures but also the decomposition behaviors differ from one metal precursor to another. Therefore, one of the most important considerations to produce thin films of high quality by the deposition of multi-component materials is to select a combination of precursors which show similar evaporation and decomposition behaviors. Particularly, because precursors containing large size metal elements such as barium and strontium show evaporation temperatures higher than those of Ti precursors by about 100° C. or more, multi-component thin films comprising Ba, St and Ti, that is, BST thin films, are not formed without great difficulty by conventional deposition methods. In contrast, titanium precursors comprising ligands of the present invention are vaporized at relatively high temperatures, compared to conventional titanium precursors, with little residues remaining after evaporation. Therefore, an improvement can be brought about in the temperature window of practical deposition process when forming multi-component thin films by use of such Ti precursors of the present invention together with Ba and/or St precursors.

Additionally, the precursors comprising the ligands of the present invention are so superior in thermal properties as not to leave residues after evaporation, allowing the production of thin films of high quality excellent in surface topology and substantially free from impurities such as carbon or nitrogen.

Having generally described this invention, a further understanding can be obtained by reference to certain specific examples which are provided herein for purposes of illustration only and are not intended to be limiting unless otherwise specified.

EXAMPLE 1

Synthesis of 4-N-Isopropoxy-β-Ketoimine [$CH_3COCHCNH(CH_2CH(CH_3)OH)CH_2CH_3$]

In a branched flask was charged 30 ml of tetrahydrofuran (THF), and 31.5 mmol (3.03 g) of 3-hexyne-2-one was dissolved in the solvent. At 0° C., one equivalent (31.5 mmol, 2.36 g) of 1-amino-2-propanol was slowly added dropwise to the solution by use of a syringe, followed by addition reaction of the reactants at room temperature for 36 hours with stirring. After completion of the reaction, the solvent was removed under vacuum to afford the title compound as a yellowish solid. This was purified through recrystalization at a low temperature (−30° C.) in hexane. The purified compound was analyzed by IR and $^1$H-NMR and the results are given as follows:

IR(Nujol, υ cm$^{-1}$): $υ_{c=o}$ 1603, $υ_{c-o}$ 1091 $^1$H-NMR (CDCl$_3$): 10.88 [C(OH)CHCN], 5.02[C(OH)CHCN], 3.98 [NCH2CH(Me)OH], 3.22~3.29[NCH$_2$CH(Me)OH], 2.22 [CNCH$_2$CH$_3$], 2.03[CH$_3$CO], 1.27[CNCH$_2$CH$_3$], 1.13 [NCH$_2$CH(CH$_3$)OH]

EXAMPLE 2

Synthesis of 4-N-Ethoxy-β-Ketoimne [$CH_3COCHCNH(CH_2CH_2OH)CH_2CH_3$]

In a three-neck flask was charged 15 ml of THF, and 10 mmol (0.96 g) of 3-hexyne-2-one was dissolved in the solvent. Into the solution, one equivalent (10 mmol, 0.61 g) of ethanolamine in 10 ml of THF was slowly added dropwise at 0° C. by use of a syringe, followed by reacting the reactants at room temperature for 5 hours with stirring. After completion of the reaction, the solvent was removed under vacuum to afford the title compound as a solid. This was purified through recrystalization at a low temperature (−30° C.) in hexane. The purified compound was analyzed by IR and $^1$H-NMR and the results are given as follows:

IR(KBr pellet, cm$^{-1}$): $υ_{OH}$ 3282, $υ_{c=o}$ 1605, 1547, $υ_{c-o}$ 1174 $^1$H-NMR(CDCl$_3$): 1.12[CNCH$_2$CH$_3$], 2.12[CH$_3$C(O) CHCN], 2.36[CNCH$_2$CH$_3$], 3.36[CNCH$_2$CH$_2$OH], 3.73 [CNCH$_2$CH$_2$OH], 3.79[CNCH$_2$CH$_2$OH], 4.96 [CH$_3$COCHCN], 10.74[CH$_3$COHCH]

EXAMPLE 3

Synthesis of 4-N,N'-Diethoxy-β-Ketoimine [$CH_3COCHCN(CH_2CH_2OH)_2CH_2CH_3$]

In a three-neck flask was charged 30 ml of THF, and 1.1 mol (1.27 ml) of 3-hexyne-2-one was dissolved in the solvent. At 0° C., 1.0 mol (2.16 ml) of diethanol amine was slowly added dropwise to the solution by use of a syringe, followed by reacting the reactants for 1 hour during temperature elevation to room temperature and for an additional hour at room temperature with stirring. After completion of the reaction, the solvent was removed under vacuum to afford the title compound as a solid. This was recrystallized at a low temperature (−30° C.) in hexane. The purified compound was analyzed by IR and $^1$H-NMR and the results are given as follows:

IR(Nujol υ cm$^{-1}$): $υ_{c=o}$ 1595, $υ_{c-o}$ 1138 $^1$H-NMR (CH$_3$OD) 5.20[COCHCN], 3.74[CN(CH$_2$CH$_2$OH)$_2$], 3.53 [CN(CH$_2$CH$_2$OH)$_2$], 3.08[CNCH$_2$CH$_3$], 2.02[CH$_3$CO], 1.12 [CNCH$_2$CH$_3$]

EXAMPLE 4

Synthesis of Ti [$CH_3COCHCNH(CH_2CH(CH_3)OH)CH_2CH_3$]$_2$

In 50 ml of THF was dissolved 2.9 mmol (0.5 g) of 4-N-isopropoxy-β-ketoimine prepared in Example 1, and 1.45 mmol (0.32 g) of Ti(OiPr)$_4$ was slowly added dropwise at 0° C. to the solution with the aid of a syringe, followed by reaction at room temperature for 24 hours with stirring. The solid phase thus formed was separated from the solvent by vacuum distillation and recrystallized with hexane. The purified metal complex was subjected to IR and $^1$H-NMR spectroscopic analyses and the results are given as follows:

IR(Nujol υ cm$^{-1}$): $υ_{c=o}$ 1601, $υ_{c-o}$ 1112 $^1$H-NMR (CDCl$_3$): 5.23[COCHCN], 4.83~4.93[COCHCN], 3.85~4.0 [NCH$_2$CH(Me)O], 3.64~3.60[NCH$_2$CH(Me)O], 2.34 [CNCH$_2$CH$_3$], 1.90[CH$_3$CO], 1.23[CNCH$_2$CH$_3$], 1.20 [NCH$_2$CH(CH$_3$)OH]

The metal complex was found to have a solubility of 0.6 mol/L in n-butyl acetate, a representative solvent for liquid delivery chemical vapor deposition.

Additionally, the metal complex was subjected to thermal gravimetric analysis and the results are shown in FIG. 1. As seen in the thermogram, the metal complex started to melt at 130° C. at atmospheric pressure and was almost completely vaporized or decomposed at 290° C., while leaving little residue.

EXAMPLE 5

Synthesis of Ti[$CH_3COCHCNH(CH_2CH_2OH)CH_2CH_3$]$_2$

In 50 ml of THF was dissolved 7.24 mmol (1.14 g) of 4-N-ethoxy-β-ketoimine prepared in Example 2, and 3.6 mmol (1.03 g) of Ti(OiPr)$_4$ was slowly added dropwise at 0° C. to the solution with the aid of a syringe. Thereafter, reaction was allowed to proceed at room temperature for 24 hours with stirring to give a solid phase. Removal of the solvent form the solution by vaccum distillation left the metal complex. This was purified through recrystallization in hexane. The purified metal complex was subjected to IR and $^1$H-NMR spectroscopic analyses and the results are given as follows:

IR(KBr pellet, cm$^{-1}$): $υ_{c=o}$ 1593, 1510, $υ_{c-o}$ 1216 $^1$H-NMR(CDCl$_3$) 1.17[CNCH$_2$CH$_3$], 2.04[CH$_3$C(O) CHCN], 2.39[CNCH$_2$CH$_3$], 3.98[CNCH$_2$CH$_2$OH] 4.11 [CNCH$_2$CH$_2$OH] 4.48[CNCH$_2$CH$_2$OH] 5.39 [CH$_3$COCHCN]

The metal complex was found to have a solubility of 0.6 mol/L in n-butyl acetate, a representative solvent for liquid delivery chemical vapor deposition.

Figure 2:
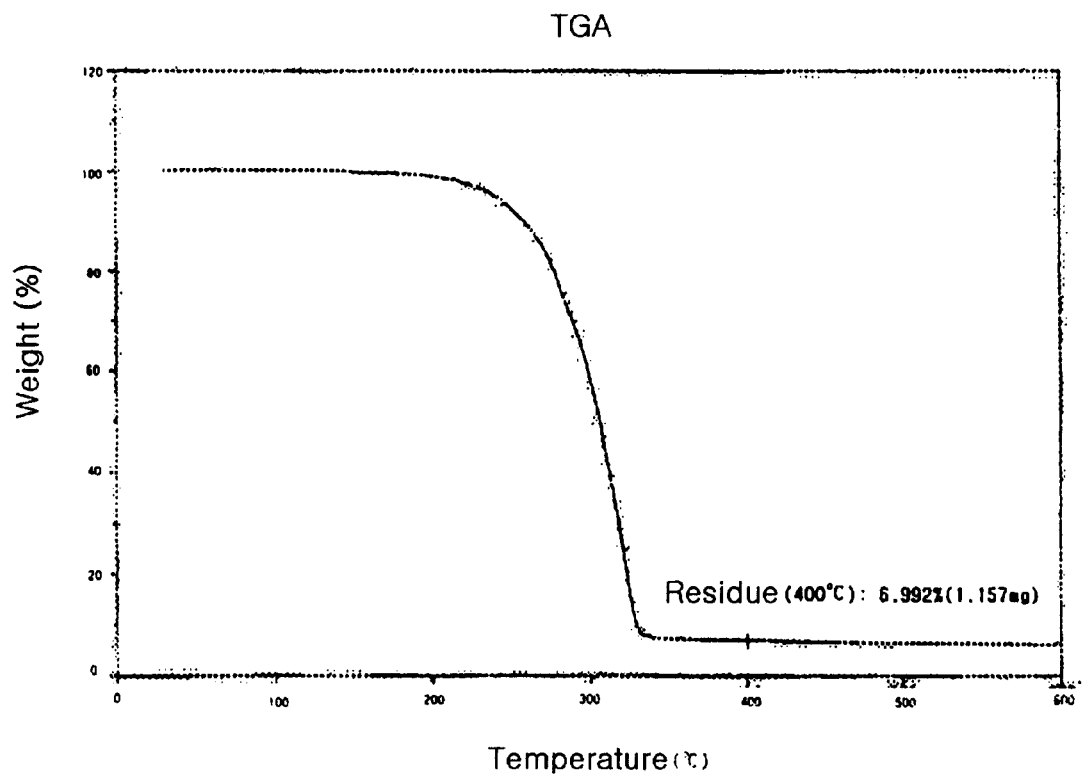
FIG. 2 is a graph showing the thermal properties of the metal complex of Example 5 as analyzed by thermal gravimetry.

Additionally, the metal complex was subjected to thermal gravimetric analysis and the results are shown in FIG. 2. As seen in the thermogram, the metal complex started to melt at 200° C. at atmospheric pressure and was vaporized or decomposed at about 330° C., while leaving solid residue in an amount of as low as 7%.

EXAMPLE 6

Synthesis of Ti[CH$_3$COCHCN(CH$_2$CH$_2$OH)$_2$ CH$_2$CH$_3$]$_2$

In a three-neck flask was charged 30 ml of THF and 3.73 mmol (0.71 g, 0.41 ml) of TiCl$_4$ was slowly dropped into the solvent by use of a syringe with maintaining an inert condition for TiCl$_4$. In a separate flask, 7.46 mmol (1.5 g) of 4-N,N'-diethoxy-β-ketoimine synthesized in Example 3 was dissolved in 30 ml of THF. This solution was added dropwise to the solution of TiCl$_4$ in THF with the aid of a syringe to give a yellowish precipitate, after which additional 10 ml of THF was added to make the solution clear. Under this condition, reaction was allowed to proceed at room temperature for 2 days with stirring. The solvent was removed by vacuum distillation to leave the solid product which was then purified by recrystallization with hexane. The purified metal complex was analyzed by IR and $^1$H-NMR and the results are given as follows:

IR(Nujol, υcm$^{-1}$): υ$_{c=o}$ 1590, υ$_{c-o}$ 1178 $^1$H-NMR (CH$_3$OD): 5.83[COCHCN], 4.17[CN(CH$_2$CH$_2$O)$_2$], 3.59 [CN(CH$_2$CH$_2$O)$_2$], 2.75[CNCH$_2$CH$_3$], 1.17[CH$_3$CO], 1.01 [CNCH$_2$CH$_3$]

The metal complex was found to have a solubility of 0.3 mol/L in n-butyl acetate. Thermal gravimetric analysis showed that the metal complex started to melt at 130° C. at atmospheric pressure and was vaporized or decomposed at about 380° C., while leaving solid residue in an amount of about 12% (data not shown).

As described hereinbefore, the metal complexes comprising the asymmetric β-ketoiminate compounds of the present invention as ligands show volatility suitable for use in the formation of thin films through chemical vapor deposition, as well as having excellent thermal properties of leaving little residues after evaporation. With great chemical stability, the metal complexes do not undergo side reactions when used with other precursors or during delivery in an evaporated state. Also, the metal complexes are not susceptible to moisture so that they are easy to handle and store. Additionally, they are very useful as precursors for use in liquid delivery chemical vapor deposition owing to their superiority in terms of solubility in organic solvents. Furthermore, titanium precursors containing the ligands of the present invention are volatilized at higher temperatures than are conventional titanium precursors, thereby greatly improving the process window upon the preparation of BST thin films using precursors of barium and strontium therewith.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. An assymetric β-ketoiminate ligand compound, represented by the following chemical formula (4):

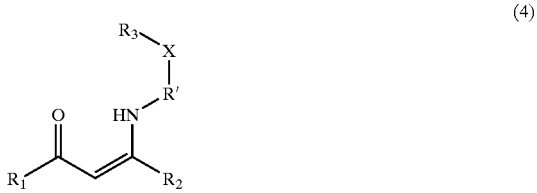

(4)

wherein R$_1$ is a linear or branched alkyl group containing 1 to 8 carbon atoms;

R$_2$ is a linear or branched alkyl group containing 2 to 9 carbon atoms, with the proviso that R$_2$ contains more carbon atoms than R$_1$;

R' is a linear or branched alkylene group containing 1 to 8 carbon atoms or a hydrocarbon containing 1 to 3 ethylene ether or propylene ether moieties, represented by —(CH$_2$)$_n$O—(n=2 or 3);

R$_3$ is a hydrogen atom; and

X is an oxygen atom or a sulfur atom.

2. A method for preparing the asymmetric β-ketoiminate ligand compound of claim 1, comprising the step of reacting an α,β-yne-one compound represented by the following chemical formula (1);

(1)

wherein, R$_1$ is a linear or branched alkyl group containing 1 to 8 carbon atoms;

and

R$_2$ is a linear or branched alkyl group containing 2 to 9 carbon atoms, with the proviso that R$_2$ contains more carbon atoms than R$_1$, with a primary amine represented by the following chemical formula (2) or with a secondary amine represented by the following chemical formula (3):

R$_3$X—R'—NH$_2$ (2)

(R$_3$X—R')$_2$—NH (3)

wherein, R' is a linear or branched alkylene group containing 1 to 8 carbon atoms or a hydrocarbon containing 1 to 3 ethylene ether or propylene ether moieties, represented by —(CH$_2$)$_n$O— (n=2 or 3);

R$_3$ is a hydrogen atom or a linear or branched alkyl group containing 1 to 9 carbon atoms; and X is an oxygen atom or a sulfur atom.

3. An organometallic precursor, prepared by the reaction of the β-ketoiminate ligand compound of claim 1 with metal.

4. The organometallic precursor according to claim 3, wherein said metal is selected from the group consisting of Ti, Zr and Hf.

* * * * *